United States Patent [19]

Lowe et al.

[11] Patent Number: 4,520,101
[45] Date of Patent: May 28, 1985

[54] PRODUCTION OF CEPHALOSPORIN C

[75] Inventors: David A. Lowe, Jamesville; Guna Romancik, Syracuse; Leonardo M. Cappelletti, Fayetteville; Richard P. Elander, Manlius, all of N.Y.

[73] Assignee: Bristol-Myers Company, New York, N.Y.

[21] Appl. No.: 472,444

[22] Filed: Mar. 7, 1983

[51] Int. Cl.$^3$ .................. C12P 35/06; C12N 9/18
[52] U.S. Cl. ...................................... 435/49; 435/197
[58] Field of Search ................................ 435/49, 197

[56] References Cited

U.S. PATENT DOCUMENTS 3,573,296  7/1968  Johnson et al. .
3,830,809  8/1974  Brooks et al. .
3,932,392  1/1976  Johnson et al. .
4,059,573 11/1977  Robinson et al. .

FOREIGN PATENT DOCUMENTS 820422   9/1959  United Kingdom .
  938755  10/1963  United Kingdom .
  975393  11/1964  United Kingdom .
  975394  11/1964  United Kingdom .
 1109362   4/1968  United Kingdom .
 1389714   4/1975  United Kingdom .
 1400433   7/1975  United Kingdom .
 1488822  10/1977  United Kingdom .
 1488821  10/1977  United Kingdom .
 1503851   3/1978  United Kingdom .
2021640A  12/1979  United Kingdom .

OTHER PUBLICATIONS

Hochster et al., Metabolic Inhibitors, vol. II, Academic Press, pp. 224–229 (1963).
Snell, Biosynthesis of Antibiotics, vol. I, Academic Press, pp. 77–79 (1966).
Jeffery et al., Biochem. J., vol. 81, 1961, pp. 591–596.
Pisano et al., Develop. Ind. Microbiol., vol. 8, 1967, pp. 417–423.
Nuesch et al., Second International Symp. on Genetics of Industrial Microorganisms (K. D. Macdonald, Ed.) pp. 451–472, Academic Press, New York, 1975.
Fujisawa et al., Agr. Biol. Chem., vol. 39, No. 6, 1975, pp. 1303–1309.
Brannon et al., Antimicrob. Agents Chemother., vol. 1, 1972, pp. 237–241.
Huber et al., Applied Microbiol., vol. 16, No. 7, 1968, pp. 1011–1014.
Liersch et al., Second International Symp. on Genetics of Industrial Microorganisms (K. D. Macdonald, Ed.) pp. 179–195, Academic Press, New York, 1975.
Felix et al., FEMS Microbiol. Lett., vol. 8, 1980, pp. 55–58.

Primary Examiner—Alvin E. Tanenholtz
Attorney, Agent, or Firm—David M. Morse

[57] ABSTRACT

Production of undesired desacetylcephalosporin C during fermentation of cephalosporin C-producing microorganisms is substantially reduced by addition of certain phosphorous compounds to the culture medium.

15 Claims, No Drawings

PRODUCTION OF CEPHALOSPORIN C

BACKGROUND OF THE INVENTION

1. Field of the Invention

This invention relates to an improved process for the production of cephalosporin C. More particularly, the invention relates to the addition of certain organic and inorganic phosphorous compounds to the culture medium during fermentation of a cephalosporin C-producing microorganism which also produces undesired desacetylcephalosporin C. Addition of the phosphorous compounds greatly inhibits formation of the desacetylcephalosporin C impurity, thus facilitating recovery of the cephalosporin C from the fermentation broth and its subsequent conversion to 7-aminocephalosporin acid (7-ACA).

2. Description of the Prior Art

Cephalosporin C [3-acetoxymethyl-7β-(D-5-amino-5-carboxypentanamido)ceph-3-em-4-carboxylic acid] is a compound which, while having some antibiotic activity per se, is of primary importance as a starting material for preparation of semi-synthetic cephalosporin antibiotics. Thus, cephalosporin C may be converted by known methods to 3-acetoxymethyl-7β-aminoceph-3-em-4-carboxylic acid (7-ACA) which is then used as a key intermediate for preparation of a wide variety of commercial cephalosporin antibiotics.

It is known that cephalosporin C may be obtained by fermentation of various microorganisms including especially fungi of the genera Emericellopsis-Cephalosporium. Illustrative of cephalosporin C-producing microorganisms are the original Brotzu strain of Cephalosporium, i.e. Cephalosporium sp. I.M.I. 49137 (ATCC 11550), and mutants thereof such as mutant strain 8650 (ATCC 14553), described in U.K. Pat. No. 1,109,362, Cephalosporium sp. I.B.I. 1131 described in U.K. Pat. No. 1,503,851 and Cephalosporium sp. strain F.12 (ATCC 20339) described in U.K. Pat. No. 1,400,433. Other examples of cephalosporin C-producing organisms reported in the literature include *Cephalosporium polyaleurum* Y-505 (FERM-P No. 1160) described in U.K. Pat. No. 1,488,822, *Cephalosporium acremonium* K-121 (ATCC 20427) and *Cephalosporium acremonium* N-75 (ATCC 20428) described in U.K. Pat. No. 1,488,821 and *Cephalosporium polyaleurum* 199 (ATCC 20359) and a mutant thereof identified as Y-505 (ATCC 20360) described in U.K. Pat. No. 1,389,714. Cephalosporin C is generally produced on an industrial scale by use of a high-producing mutant strain of *Cephalosporium acremonium* (also known as *Acremonium chrysogenum*). Examples of such mutants and methods for their preparation have been extensively described in the literature.

Despite exhaustive research over the years, fermentation of cephalosporin C on a commercial scale is still not entirely satisfactory. Most cephalosporin C-producing microorganisms, especially those high producing strains used in commercial production, result in co-production of a significant proportion of desacetylcephalosporin C, an impurity which is extremely difficult to separate from the desired cephalosporin C product because of its similar chemical and physical characteristics. Presence of the desacetylcephalosporin C, typically in amounts of about 15% of the total cephalosporin nucleus produced during fermentation, results in recovery of cephalosporin C (or more commonly, a solvent-extractable derivative thereof) contaminated with desacetylcephalosporin C (or derivative thereof). Moreover, since on an industrial scale the cephalosporin C (or derivative thereof) is usually not purified prior to subsequent conversion to 7-ACA, product quality of the 7-ACA is also adversely affected by the concomitant production of desacetylcephalosporin C in the initial fermentation broth.

The prior art dealing with cephalosporin C production is primarily concerned with finding new microorganisms of higher cephalosporin C productivity and providing fermentation additives which increase cephalosporin C production. Thus, for example, mutant strains of *Cephalosporium acremonium* have been developed which produce substantially higher yields of cephalosporin C. It has been suggested to add various additives to the nutrient medium during fermentation of a cephalosporin C-producing organism so as to increase the cephalosporin C yield. Thus, the use of sulfur compounds such as sodium sulfite, sodium metabisulphite, sodium thiosulfate, sodium hydrosulphite, sodium thiosulphate and sodium sulphate are disclosed in U.K. Pat. No. 820,422, use of methionine, calcium chloride, magnesium chloride, ammonium sulfate and certain carbohydrates, oils and fatty acids is disclosed in U.K. Pat. No. 938,755, use of norvaline and norleucine is disclosed in U.K. Pat. No. 975,393, use of phenylacetic acid is disclosed in U.K. Pat. No. 975,394 and use of ε-caprolactam, 2-butanone, secondary butyl alcohol and 1,3-butanediol is disclosed in U.K. Pat. No. 1,503,851. The problem of co-production of desacetylcephalosporin C during cephalosporin C fermentation has been addressed only in terms of providing microorganisms which produce higher proportions of cephalosporin C nucleus as cephalosporin C or in terms of extraction-/isolation procedures (e.g. U.S. Pat. No. 4,059,573).

Desacetylcephalosporin C was first detected in culture filtrates of *Cephalosporium acremonium*. Abraham et al. proposed that formation of this substance was due to the enzymatic deacetylation of cephalosporin C (*Biochem. J.* 81: 591–596, 1961). Subsequently, esterase enzymes capable of deacetylating cephalosporin C have been isolated from a variety of sources, for example, citrus fruits, bacteria, actinomycetes, wheat germ, mammalian liver and kidney and *Rhodotorula*. Pisano et al. in *Develop. Ind. Microbiol.* 8: 417–423, 1967, report that esterase activity is widespread in the genus Cephalosporium. The majority of these acetylesterase enzymes appear to have broad substrate tolerances, i.e. β-naphthyl acetate and triacetin are active substrates, and their activity toward cephalosporin C does not appear unique.

Nuesch et al. in *Second International Symp. on Genetics of Industrial Microorganisms, Proc.*, 1975, ed. MacDonald, K. D., New York, Academic Press, pg. 451–472 and Fujisawa et al. in *Agr. Biol. Chem.* 39(6): 1303–1309 (1975) independently partially purified cephalosporin C esterase activity from extracellular broth supernatant of *Cephalosporium acremonium* and concluded that the presence of the enzyme activity was partially responsible for the occurrence of desacetylcephalosporin C in *C. acremonium* fermentations. Similar esterase activity has been detected in the cephalosporin C producing Streptomycetes *Streptomyces clavuligerus* (*Antimicrob. Agents Chemother.* 1: 237–241, 1972). Huber in *Appl. Microbiol.* 16(7): 1011–1014 (1968), however, has presented evidence that the formation of desacetylcephalosporin C during the fermentation process is due to the non-enzymatic hydrolysis of cephalosporin C. It is the opinion of the present inventors that desacetylcephalosporin C formation is due to both enzymatic and non-enzymatic hydrolysis, with enzymatic acetylesterase activity playing a significant role.

Reports by Liersch et al. in *Second International Symp. on Genetics of Industrial Microorganisms*, Proc., 1976, ed. MacDonald, K. D., New York, Academic Press, pg. 179–195 and Felix et al. in *FEMS Microbiol. Lett.* 8: 55–58, 1980 have indicated that desacetylcephalosporin C is also an intracellular intermediate in the biosynthesis of cephalosporin C from desacetoxycephalosporin C.

The enzyme activity of the partially purified acetylesterase from *Cephalosporium acremonium* was reported to be inhibited by diisopropylfluorophosphate, a recognized inhibitor of esterases (*Agr. Biol. Chem.* 39(6): 1303–1309, 1975). The extreme toxicity and high cost of this phosphorous acetylesterase inhibitor, however, prevents its use in the commercial production of cephalosporin C.

Cephalosporin C, because of its amphoteric nature, is normally converted into a derivative so that it can be more easily recovered from the fermentation broth by solvent extraction procedures. Examples of such derivatives are given in U.K. patent application No. 2,021,640A. One particularly preferred process is disclosed in U.S. Pat. No. 3,573,296. The cephalosporin C derivative obtained by such preferred process may be recovered as a crystalline bis-dicyclohexylamine salt as disclosed in U.S. Pat. No. 3,830,809. The cephalosporin C or derivative thereof recovered from the fermentation broth is then cleaved by a conventional procedure, e.g. the process of U.S. Pat. No. 3,932,392, to provide 7-ACA.

As noted above, the desacetylcephalosporin C impurity typically obtained during fermentation in amounts of about 15% of the total cephalosporin nucleus (cephalosporin C and desacetylcephalosporin C) has chemical and physical characteristics quite similar to those of the desired cephalosporin C product. Thus, when the cephalosporin C is converted to a solvent-extractable derivative, the desacetylcephalosporin C is also converted to a similar derivative and the cephalosporin C derivative then isolated is contaminated with the desacetylcephalosporin C derivative. It can be seen, therefore, that reducing the proportion of cephalosporin nucleus obtained as desacetylcephalosporin C will result in a purer cephalosporin C derivative product. Moreover, since this derivative is not normally purified prior to conversion to 7-ACA, reduced amounts of desacetylcephalosporin C in the fermentation broth will also result in a better quality 7-ACA product.

The present invention is directed toward provision of certain phosphorous compounds which act as inhibitors of desacetylcephalosporin C production during fermentation of cephalosporin C. The resulting fermentation broth contains a significantly higher proportion of cephalosporin C to desacetylcephalosporin C, thus improving the quality of the recovered cephalosporin C product and, in turn, the quality of the ultimate 7-ACA intermediate prepared from such cephalosporin C product.

SUMMARY OF THE INVENTION

The present invention relates to an improvement in the production of cephalosporin C by submerged aerobic culture of cephalosporin C-producing microorganisms. More particularly, the present invention relates to a method of inhibiting formation of desacetylcephalosporin C during fermentation of a cephalosporin C-producing microorganism, said microorganism being one which also produces desacetylcephalosporin C, by addition of certain organic and inorganic phosphorous compounds to the culture medium.

The phosphorous compound inhibitors provided by the present invention have the general formulae

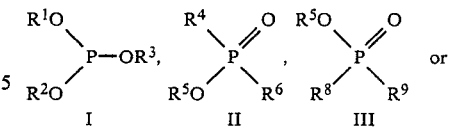

wherein $R^1$, $R^2$ and $R^3$ are each independently optionally substituted alkyl, aryl or aralkyl, $R^4$ is optionally substituted alkyl or $-OR^{10}$ in which $R^{10}$ is hydrogen or optionally substituted alkyl, aryl or aralkyl, $R^5$ is hydrogen or optionally substituted alkyl, aryl or aralkyl, $R^6$ is hydrogen, hydroxy, alkenyl, alkanoyl or optionally substituted alkyl and $R^8$ and $R^9$ are either both hydrogen or both chloro. Such compounds effectively decrease formation of desacetylcephalosporin C during fermentative production of cephalosporin C. Moreover, these compounds are substantially less nontoxic than diisopropylfluorophosphate and, in general, relatively inexpensive, thus enabling their practical use in large scale cephalosporin C production.

DETAILED DESCRIPTION

The process of the present invention is applicable to any conventional fermentative procedure for preparation of cephalosporin C, providing that such procedure utilizes a cephalosporin C-producing microorganism which also produces desacetylcephalosporin C in the fermentation broth. Many examples of such microorganisms are described in the literature, e.g. U.K. patent application No. 2,060,610A. Other cephalosporin C-producing microorganisms may be easily tested for desacetylcephalosporin C production by conventional assays well known to those skilled in the art.

The most preferred cephalosporin C-producing microorganism for use in the present invention is a strain of *Cephalosporium acremonium* (also known as *Acremonium chrysogenum*), which produces both cephalosporin C and desacetylcephalosporin C. Typical production strains of *Cephalosporium acremonium* result in formation of approximately 15% of the total cephalosporin C nucleus (cephalosporin C and desacetylcephalosporin C) as desacetylcephalosporin C.

The process of the invention will desirably be carried out by culturing a cephalosporin C-producing microorganism (one capable of producing both cephalosporin C and desacetylcephalosporin C) under aerobic conditions, preferably in submerged culture, in a conventional cephalosporin C nutrient medium according to conventional cephalosporin C fermentation procedures. The invention is in the discovery that addition of certain phosphorous compounds to the nutrient medium will substantially reduce production of desacetylcephalosporin C during fermentation and result in a final broth containing a substantially higher proportion of the desired cephalosporin C to undesired desacetylcephalosporin C.

The nutrient medium employed should contain assimilable sources of carbon and nitrogen and, if desired, growth promoting substances as well as inorganic salts.

Suitable carbon sources include, for example, glucose, sucrose, starch, soluble starch, vegetable and animal oils, dextrin and maltose.

Suitable nitrogen souces include, for example, natural nitrogen-containing substances or materials prepared from them such as meat extracts, peptone, casein, cornsteep liquor, yeast extracts, soy bean flour, tryptone, cottonseed meal and wheat bran. Nitrogen containing organic or inorganic compounds may also be used, for example, urea, nitrates and ammonium salts such as ammonium acetate, ammonium chloride or ammonium sulfate.

Inorganic salts which may be used in the fermentation medium include sulfates, nitrates, chlorides, carbonates, etc., which have been employed in cephalosporin C production.

Growth-promoting substances which may be used include, for example, cysteine, cystine, thiosulfate, methyl oleate and, in particular, methionine and also trace elements such as iron, zinc, copper and manganese.

Culturing conditions such as temperature, pH and fermentation time are selected such that the microorganism employed may accumulate a maximum amount of the desired cephalosporin C. The temperature is normally kept at about 15°–45°, preferably at about 25° C., and fermentation is carried out for a period of from about 1–20 days, preferably 4–10 days and most preferably about six days.

It has now been found that certain organic and inorganic phosphorous compounds when added to the culture medium during cultivation of a cephalosporin C-producing microorganism will result in substantially reduced production of desacetylcephalosporin C in the fermentation broth. It is believed that this reduction in desacetylcephalosporin C production results from inhibition of the acetylesterase enzyme typically produced during cultivation of cephalosporin C-producing microorganisms.

The phosphorus compounds which may be used in the process of the present invention may be represented by the formulae

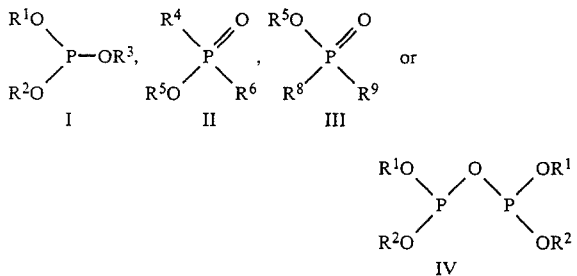

wherein $R^1$, $R^2$ and $R^3$ are each independently optionally substituted alkyl, aryl or aralkyl, $R^4$ is optionally substituted alkyl or $-OR^{10}$ in which $R^{10}$ is hydrogen or optionally substituted alkyl, aryl or aralkyl, $R^5$ is hydrogen or optionally substituted alkyl, aryl or aralkyl, $R^6$ is hydrogen, hydroxy, alkenyl, alkanoyl or optionally substituted alkyl and $R^8$ and $R^9$ are either both hydrogen or both chloro.

Preferred phosphorous compounds are those compounds of formulae I, II, III and IV wherein $R^1$, $R^2$ and $R^3$ each independently represent straight or branched chain $C_1$–$C_{10}$ alkyl, phenyl or phenyl $(C_1$–$C_4)$alkyl, said alkyl group or the alkyl portion of phenylalkyl being optionally substituted by one or more, preferably 1–3, substituents such as halo (chloro, bromo, fluoro, iodo) or carboxy and said phenyl group or the phenyl portion of phenylalkyl being optionally substituted by one or more, preferably 1–3, substituents independently selected from such groups as $C_1$–$C_6$ alkyl, $C_1$–$C_6$ alkoxy and halo, $R^4$ is $C_1$–$C_6$ alkyl optionally substituted with one or more, preferably 1–3, halo groups or $-OR^{10}$ in which $R^{10}$ is hydrogen, $C_1$–$C_{10}$ alkyl, phenyl or phenyl $(C_1$–$C_4)$alkyl, said alkyl, phenyl and phenylalkyl radicals being optionally substituted as defined above for $R^1$, $R^5$ is hydrogen, $C_1$–$C_{10}$ alkyl, phenyl or phenyl $(C_1$–$C_4)$alkyl, said alkyl, phenyl and phenylalkyl radicals being optionally substituted as defined above for $R^1$, $R^6$ is hydrogen, hydroxy, $C_2$–$C_6$ alkenyl, $C_2$–$C_6$ alkanoyl, or $C_1$–$C_6$ alkyl, said alkyl group being optionally substituted by one or more, preferably 1–3, substituents such as cyano, $C_2$–$C_6$ alkanoyl or carbo $(C_1$–$C_6)$alkoxy and $R^8$ and $R^9$ are either both hydrogen or both chloro.

Phosphite compounds of formula I may be exemplified by trimethyl phosphite, triethyl phosphite, triisopropyl phosphite, tributyl phosphite, triphenyl phosphite and tris(2-chloroethyl)phosphite. Mixed function phosphites such as benzyl diethyl phosphite and diphenyl isodecyl phosphite may also be used.

Phosphorous compounds of formula II may be exemplified by phosphorous acid, dibenzyl phosphite, dibutyl phosphite, diethyl phosphite, diisopropyl phosphite, dimethyl phosphite, diphenyl phosphite, triethyl phosphonoacetate, 2-chloroethyl phosphonic acid, diethyl cyanomethyl phosphonate, dimethyl methyl phosphonate, dimethyl phosphate, trimethyl phosphonoacetate, diethyl ethyl phosphonate, diethyl carbomethoxymethyl phosphonate, diethyl acetyl phosphonate, dimethyl acetylmethyl phosphonate, dimethyl cyanomethyl phosphonate, diethyl allyl phosphonate and 2-carboxyethyl phosphonic acid.

Compounds of general formula III may be illustrated by hypophosphorous acid, monomethylphosphonate, monoethylphosphonate and 2,2,2-trichloroethyl phosphorodichloridite.

Pyrophosphite compounds of formula IV may be illustrated by tetramethylpyrophosphite and tetraethylpyrophosphite.

Preferred phosphorous compound inhibitors include phosphorous acid, hypophosphorous acid, diisopropyl phosphite, triisopropyl phosphite, dibenzyl phosphite, dimethyl phosphite, tributyl phosphite, triethyl phosphonoacetate, 2-chloroethyl phosphonic acid, tetraethylpyrophosphite, diethyl cyanomethyl phosphonate, dimethyl methyl phosphonate, 2,2,2-trichloroethyl phosphorodichloridite, dimethyl phosphate, diphenyl phosphite, triphenyl phosphite, trimethyl phosphite, dibutyl phosphite, tris(2-chloroethyl)phosphite, trimethyl phosphonoacetate, diethyl ethyl phosphonate, diethyl carbomethoxymethyl phosphonate, diethyl acetyl phosphonate, dimethyl acetylmethyl phosphonate, dimethyl cyanomethyl phosphonate and diethyl allyl phosphonate.

Particularly preferred compounds include phosphorous acid, hypophosphorous acid, diisopropyl phosphite, triisopropyl phosphite, dibenzyl phosphite, dimethyl phosphite and tributyl phosphite.

The most preferred phosphorous compound inhibitor is phosphorous acid.

The phosphorous compounds are preferably employed so as to give final broth concentrations of from about 100 to 3000 parts per million (based on weight) and most preferably about 200 to 1000 parts per million. Inhibitor compound may be added all at once or at periodic intervals during the course of fermentation.

Most advantageously the organic phosphorous compounds are added to ongoing fermentations between about 70 and 140 hours as single or multiple shots. The inorganic phosphorous compounds may advantageously be added to ongoing fermentations immediately after inoculation to about 140 hours after inoculation. Alternatively, they may be batched into the fermentation medium before sterilization.

Use of the above-mentioned phosphorous compounds according to the process of the present invention is found to substantially lower the percentage of desacetylcephalosporin C (based on total cephalosporin nucleus which is cephalosporin C and desacetylcephalosporin C) in the fermentation broth. When used in typical cephalosporin C fermentations, levels of desacetylcephalosporin C have been reduced to about 4% of the total cephalosporin nucleus compared to about 15% in untreated fermentations.

In treated shake flask fermentations the total amount of cephalosporin nucleus produced appears to remain unchanged and thus the cephalosporin C titers are generally increased by an appropriate amount. In larger scale fermentations it has not been established that use of the phosphorous inhibitor compounds results in any increased levels of cephalosporin C. Even if cephalosporin C levels remain constant, however, the reduced quantity of desacetylcephalosporin C in treated fermentations greatly facilitates recovery of the desired cephalosporin C product in a higher state of purity.

The phosphorous compounds of the present invention were shown to have their inhibitory activity at the enzyme level. Thus, cephalosporin C esterase activity was partially purified from *Cephalosporium acremonium* broth supernatant by DEAE Sephadex A50 column chromatography and the hydrolytic activity of this preparation (as measured by HPLC by following the conversion of cephalosporin C to desacetylcephalosporin C) was found to be inhibited by phosphorous compounds of formulae I, II, III and IV.

After fermentation is complete the desired cephalosporin C product is preferably converted by known methods such as those described in U.S. Pat. No. 3,573,296 to a derivative which can be more easily recovered from the broth by solvent extraction procedures. The cephalosporin C or derivative thereof obtained from fermentation may then be converted by known methods to 7-ACA, a key intermediate in the preparation of many semi-synthetic cephalosporins. By employing the phosphorous inhibitor compounds according to the present invention, the cephalosporin C or derivative thereof and the ultimate 7-ACA intermediate are obtained more efficiently and in a greater degree of purity when compared with the prior untreated broth procedure.

The following examples are intended to illustrate the present invention without in any way limiting the scope of the invention to the embodiments specifically described. The term "ppm" used in the examples refers to a weight/weight basis.

EXAMPLE 1

Standard shake flask fermentations of *Cephalosporium acremonium* (a high ceph C-producing mutant strain which also produces desacetyl ceph C) were set up according to the following protocol. Seed culture was initiated from the inoculation of a corn steep liquor-glucose based seed medium from a frozen preservation culture. Seed flasks were cultured for three days at 28° C. while being shaken at 260 rpm, and 10% inoculum volume was used to start production stage fermentations. Production medium was based on a balanced composition of corn steep liquor, PHARMAMEDIA (cottonseed meal sold by Traders Oil Mill Company, Forth Worth, Tex.), dextrin, soy oil, methionine and ammonium sulfate. Flasks were shaken at 25° C. at 260 rpm for a total period of six days after which time portions of the broth were diluted, filtered and assayed for cephalosporin C and desacetylcephalosporin C by HPLC. Inhibitors were added at the recorded amounts at day 4 (96 hours). Results are summarized below.

| Inhibitor Added | Addition Level ppm | Ceph C mcg/g | Des Ceph C mcg/g | Des C/ Total Ceph Nucleus* (%) |
|---|---|---|---|---|
| di-isopropyl phosphite | 1600 | 9750 | 495 | 4.83 |
|  | 600 | 9850 | 520 | 5.01 |
| tri-isopropyl phosphite | 1600 | 11,000 | 575 | 4.96 |
|  | 600 | 8995 | 530 | 5.56 |
| dibenzyl phosphite | 600 | 9380 | 485 | 4.92 |
|  | 100 | 9220 | 660 | 6.68 |
| dimethyl hydrogen phosphite (from Mobil Chem. Co.) | 600 | 9400 | 350 | 3.60 |
|  | 100 | 10,615 | 520 | 4.67 |
| dimethyl hydrogen phosphite (from Alfa Chem. Co.) | 600 | 9380 | 340 | 3.49 |
|  | 100 | 9360 | 415 | 4.23 |
| diethyl acetyl phosphonate | 1000 | 9285 | 440 | 4.52 |
|  | 600 | 9665 | 445 | 4.40 |
| control no addition |  | 8760 | 705 | 7.45 |

*Ceph C + Des Ceph C

EXAMPLE 2

Using standard shake flask fermentation conditions and the same producing culture as described in Example 1, inorganic and organic phosphorous compounds were added to ongoing fermentations at 0, 48 and 96 hours after inoculation to give final inhibitor broth concentrations of 100 to 800 ppm. Results are summarized by the following data table.

| | Day 6 | | Day 7 | |
|---|---|---|---|---|
| Inhibitor Compound Hour of addition/final conc. in ppm | Ceph C/ Des Ceph C in mcg/g | *D C + D % | Ceph C/ Des Ceph C in mcg/g | *D C + D % |
| phosphorous acid | | | | |

-continued

| Inhibitor Compound Hour of addition/final conc. in ppm | Day 6 | | Day 7 | |
|---|---|---|---|---|
| | Ceph C/ Des Ceph C in mcg/g | *D $\frac{}{C + D}$ % | Ceph C/ Des Ceph C in mcg/g | *D $\frac{}{C + D}$ % |
| 0/hour/100 | 11,810/730 | 5.8 | 10,300/925 | 8.2 |
| 200 | 10,540/460 | 4.2 | 11,585/935 | 7.4 |
| 400 | 9,940/350 | 3.4 | 10,240/500 | 4.6 |
| 800 | 10,600/390 | 3.5 | 10,335/425 | 3.9 |
| 48 hour/100 | 10,300/710 | 6.4 | 9,370/820 | 8.0 |
| 200 | 9,895/535 | 5.1 | 9,950/710 | 6.6 |
| 400 | 10,030/405 | 3.8 | 9,305/480 | 4.9 |
| 800 | 9,200/355 | 3.7 | 9,180/470 | 4.8 |
| 96 hour/100 | 8,355/755 | 8.3 | 10,240/1,430 | 12.2 |
| 200 | 7,670/670 | 8.0 | 9,605/975 | 9.2 |
| 400 | 7,830/640 | 7.5 | 8,645/705 | 7.5 |
| 800 | 10,140/780 | 7.1 | 8,225/770 | 8.5 |
| diphenylphosphite | | | | |
| 96/hour/100 | 10,565/1,145 | 9.7 | 9,705/1,220 | 11.2 |
| 200 | 10,345/935 | 8.2 | 10,000/1,410 | 12.3 |
| 400 | 9,985/690 | 6.4 | 9,250/945 | 9.2 |
| 800 | 9,615/780 | 7.5 | 8,800/720 | 7.5 |
| Control (no inhibitor addition) | 8,055/1,145 | 12.5 | 8,784/1,562 | 15.1 |

* $\frac{\text{conc. des ceph C}}{\text{conc. ceph C + des ceph C}} \times 100$

EXAMPLE 3

Using standard shake flask fermentation conditions and the same producing culture as described in Example 1, inorganic phosphorous inhibitor compounds were added to the medium prior to sterilization by autoclaving at 121° C. for 20 minutes. Results are summarized by the following data table.

| | Day 6 | |
|---|---|---|
| Inhibitor compound/ final conc. in ppm | Ceph C/ Des Ceph C in mcg/g | *D $\frac{}{C + D}$ % |
| phosphorous acid/200 | 9,740/600 | 5.8 |
| 400 | 8,050/340 | 4.0 |
| 800 | 7,111/285 | 3.8 |
| hypophosphorous acid/150 | 8,110/1,130 | 12.2 |
| 300 | 8,600/1,000 | 10.4 |
| 450 | 9,080/940 | 9.4 |
| Control (no inhibitor addition) | 7,840/1,060 | 11.9 |

* $\frac{\text{conc. des ceph C}}{\text{conc. ceph C + des ceph C}} \times 100$

EXAMPLE 4

*Cephalosporium acremonium* was fermented in 30 liter stirred tank fermentators according to standard procedures for culture buildup and fermentation. The vessels were inoculated at 10% of the medium volume with a seed culture proparged on a corn steep liquor-PHARMAMEDIA-glucose medium. The fermentation medium was composed of corn steep liquor, soyflour and soy oil as organic carbon and nitrogen. Glucose syrup and soy oil were fed during the fermentation. To the test fermentor tributylphosphite was added at 96 hours to a final broth concentration of 300 ppm. The effect of the addition is recorded below in terms of changes in the levels of cephalosporin C and desacetylcephalosporin C.

Tributylphosphite-300 ppm at 96 h.

| Time (hours) | *D $\frac{}{C + D}$ % |
|---|---|
| 74 | 4.2 |
| 85 | 3.7 |
| 98 | 4.3 |
| 109 | 4.0 |
| 122 | 4.6 |
| 133 | 5.8 |
| 146 | 6.9 |
| 157 | 7.9 |
| 170 | 9.1 |

* $\frac{\text{conc. des ceph C}}{\text{conc. ceph C + des ceph C}} \times 100$

Control run—no inhibitor needed

| Time (hours) | *D $\frac{}{C + D}$ % |
|---|---|
| 74 | 4.8 |
| 85 | 4.5 |
| 98 | 5.1 |
| 109 | 6.9 |
| 122 | 8.9 |
| 133 | 12.6 |
| 146 | 13.0 |
| 157 | 13.2 |
| 170 | 15.0 |

The addition of tributyl phosphite lowered the amount of desacetylcephalosporin C produced to 9.1% of the total ceph nucleus compared to 15.0% in the control run.

EXAMPLE 5

*Cephalosporium acremonium* was fermented in a 3000 liter stirred tank fermentor using conventional cephalosporin C media and conventional procedures. Dimethyl hydrogen phosphite was added at 100 hours to a final broth concentration of 600 ppm. The results of inhibitor addition are summarized in the following tables.

Dimethyl hydrogen phosphite at 100 hours

| Time (hours) | $\frac{*D}{C+D}$ (%) |
|---|---|
| 78 | 5.8 |
| 91 | 7.4 |
| 102 | 8.8 |
| 115 | 7.7 |
| 126 | 6.9 |
| 139 | 7.9 |
| 150 | 7.4 |
| 163 | 8.3 |
| 168 | 9.0 |

* $\frac{\text{conc. des ceph C}}{\text{conc. ceph C + des ceph C}} \times 100$

Control—no inhibitor needed

| Time (hours) | $\frac{*D}{C+D}$ (%) |
|---|---|
| 83 | 5.8 |
| 96 | 8.2 |
| 107 | 10.7 |
| 120 | 11.9 |
| 131 | 13.8 |
| 144 | 16.9 |
| 155 | 18.9 |
| 168 | 20.9 |
| 170 | 22.5 |

* $\frac{\text{conc. des ceph C}}{\text{conc. ceph C + des ceph C}} \times 100$

EXAMPLE 6

The following additional phosphorous compounds were also tested in shake flask fermentations and exhibited inhibitory activity with respect to desacetylcephalosporin C production:
triethyl phosphonoacetate
2-chloroethyl phosphonic acid
tetraethylpyrophosphite
diethyl cyanomethyl phosphonate
2,2,2-trichloroethyl phosphorodichloridite
dimethyl phosphate
trimethyl phosphite
triethyl phosphite
dibutyl phosphite
tris(2-chloroethyl)phosphite
trimethyl phosphonoacetate
diethyl ethyl phosphonate
tributyl phosphite
triphenyl phosphite
diethyl carbomethoxymethyl phosphonate
dimethyl acetylmethyl phosphonate
dimethyl cyanomethyl phosphonate
diethyl allyl phosphonate

EXAMPLE 7

The following additional phosphorous compounds were also tested in fermentors and exhibited inhibitory activity with respect to desacetylcephalosporin C production:
triethyl phosphonoacetate
2-chloroethyl phosphonic acid
tetraethylpyrophosphite
diethyl cyanomethyl phosphonate
dimethyl methyl phosphonate
2,2,2-trichloroethyl phosphorodichloridite
dimethyl phosphate
triethyl phosphite
diphenyl phosphite
triphenyl phosphite
diisopropyl phosphite
triisopropyl phosphite

We claim:

1. In a method for producing cephalosprin C by culturing a cephalosporin C-producing microorganism which also produces desacetylcephalosporin C in a nutrient medium, the improvement which comprises adding to said medium a phosphorous compound of the formula

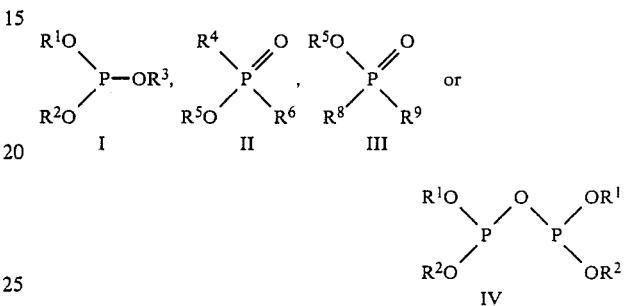

wherein $R^1$, $R^2$ and $R^3$ each independently represent straight or branched chain $C_1$–$C_{10}$ alkyl, phenyl or phenyl($C_1$–$C_4$)-alkyl, said alkyl group or the alkyl portion of phenylalkyl being optionally substituted by one or more halo or carboxy substituents and said phenyl group or the phenyl portion of phenylalkyl being optionally substituted by one or more $C_1$–$C_6$ alkyl, $C_1$–$C_6$ alkoxy or halo substituents; $R^4$ is $C_1$–$C_6$ alkyl optionally substituted by one or more halo groups or is —$OR^{10}$ in which $R^{10}$ is hydrogen or is as defined above for $R^1$; $R^5$ is hydrogen or is as defined above for $R^1$; $R^6$ is hydrogen, $C_2$–$C_6$ alkenyl, $C_2$–$C_6$ alkanoyl or $C_1$–$C_6$ alkyl, said alkyl group being optionally substituted by one or more cyano, $C_2$–$C_6$ alkanoyl or carbo ($C_1$–$C_6$) alkoxy radicals; and $R^8$ and $R^9$ are either both hydrogen or are both chloro, in a concentration of from about 100 to 3000 parts per million.

2. The method according to claim 1 wherein the microorganism is a cephalosporin C-producing strain of the genus Cephalosporium.

3. The method according to claim 1 wherein the microorganism is a cephalosporin C-producing strain of *Cephalosporium acremonium*.

4. The method according to claim 1, 2 or 3 wherein the phosphorous compound has the formula

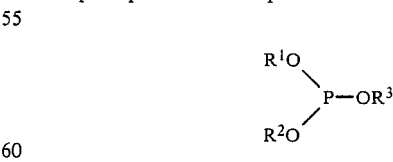

wherein $R^1$, $R^2$ and $R^3$ are each independently $C_1$–$C_{10}$ alkyl, halo-substituted $C_1$–$C_{10}$ alkyl, phenyl or benzyl.

5. The method according to claim 4 wherein $R^1$, $R^2$ and $R^3$ are each independently methyl, ethyl, isopropyl, n-butyl, phenyl, benzyl, isodecyl or 2-chloroethyl.

6. The method according to claim 1, 2, or 3 wherein the phosphorous compound has the formula

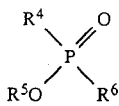

wherein $R^4$ is $C_1$–$C_6$ alkyl, halo-substituted $C_1$–$C_6$ alkyl or is —$OR^{10}$ in which $R^{10}$ is hydrogen, $C_1$–$C_{10}$-alkyl, halo-substituted $C_1$–$C_{10}$ alkyl, phenyl or benzyl; $R^5$ is hydrogen, $C_1$–$C_{10}$ alkyl, halo-substituted $C_1$–$C_{10}$ alkyl, phenyl or benzyl; and $R^6$ is hydrogen, $C_2$–$C_6$ alkenyl, $C_1$–$C_6$ alkyl, $C_2$–$C_6$ alkanoyl or $C_1$–$C_6$ alkyl substituted by $C_2$–$C_6$ alkanoyl, carbo ($C_1$–$C_6$) alkoxy or cyano.

7. The method according to claim 6 wherein $R^4$ is 2-chloroethyl or —$OR^{10}$ is which $R^{10}$ is hydrogen, benzyl, n-butyl, ethyl, isopropyl, methyl, phenyl or 2,2,2-trichloroethyl; $R^5$ is hydrogen, ethyl, methyl, 2-chloroethyl, n-butyl, phenyl, isopropyl or benzyl; and $R^6$ is hydrogen, allyl, cyanomethyl, carboethoxymethyl, methyl, carbomethoxymethyl, ethyl, acetyl or acetylmethyl.

8. The method according to claim 1, 2 or 3 wherein the phosphorous compound has the formula

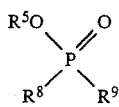

wherein $R^5$ is hydrogen, $C_1$–$C_{10}$ alkyl, halo-substituted $C_1$–$C_{10}$ alkyl, phenyl or benzyl; and $R^8$ and $R^9$ are either both hydrogen or both chloro.

9. The method according to claim 8 wherein $R^5$ is hydrogen, methyl, ethyl or 2,2,2-trichloroethyl.

10. The method according to claim 1, 2 or 3 wherein the phosphorous compound is tetramethylpyrophosphite or tetraethylpyrophosphite.

11. The method according to claim 1, 2, or 3 wherein the phosphorous compound is selected from the group consisting of phosphorous acid, hypophosphorous acid, diisopropyl phosphite, triisopropyl phosphite, dibenzyl phosphite, dimethyl phosphite, tributyl phosphite, triethyl phosphonoacetate, tetraethylpyrophosphite, diethyl cyanomethyl phosphonate, dimethyl methyl phosphonate, 2,2,2-trichloroethyl phosphorodichloridite, diphenyl phosphite, triphenyl phosphite, trimethyl phosphite, dibutyl phosphite, tris(2-chloroethyl)phosphite, trimethyl phosphonoacetate, diethyl ethyl phosphonate, diethyl carbomethoxymethyl phosphonate, diethyl acetyl phosphonate, dimethyl acetyl methyl phosphonate, dimethyl cyanomethyl phosphonate and diethyl allyl phosphonate.

12. The method according to claim 1, 2 or 3 wherein the phosphorous compound is selected from the group consisting of phosphorous acid, hypophosphorous acid, diisopropyl phosphite, triisopropyl phosphite, dibenzyl phosphite, dimethyl phosphite and tributyl phosphite.

13. The method according to claim 1, 2 or 3 wherein the phosphorous compound is phosphorous acid.

14. The method according to claim 1, 2 or 3 wherein an organic phosphorous compound is added to the ongoing fermentation between about 70 to 140 hours after inoculation.

15. The method according to claim 1, 2 or 3 wherein an inorganic phosphorous compound is added to the culture medium prior to sterilization or from 0 to 140 hours after inoculation.

* * * * *